(12) United States Patent
Sana et al.

(10) Patent No.: US 7,534,561 B2
(45) Date of Patent: May 19, 2009

(54) NUCLEIC ACID ARRAY IN SITU FABRICATION METHODS AND ARRAYS PRODUCED USING THE SAME

(75) Inventors: Theodore R. Sana, San Mateo, CA (US); Eric M. Leproust, Campbell, CA (US); Michel G. M. Perbost, Bethany, CT (US); Paul K. Wolber, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 547 days.

(21) Appl. No.: 10/407,080

(22) Filed: Apr. 2, 2003

(65) Prior Publication Data

US 2004/0197781 A1 Oct. 7, 2004

(51) Int. Cl.
*C12Q 1/68* (2006.01)
*C12N 11/16* (2006.01)
*C07H 21/04* (2006.01)
*C12P 19/34* (2006.01)

(52) U.S. Cl. .................. 435/6; 435/91.1; 435/283.1; 435/287.2; 536/23.1; 536/25.3

(58) Field of Classification Search .............. None
See application file for complete search history.

(56) References Cited

U.S. PATENT DOCUMENTS

| | | | |
|---|---|---|---|
| 4,087,672 A | 5/1978 | Yi | |
| 4,545,018 A | 10/1985 | Clements et al. | |
| 4,825,034 A | 4/1989 | Auvert et al. | |
| 4,866,243 A | 9/1989 | Sakane et al. | |
| 4,868,126 A | 9/1989 | Schwartz | |
| 4,918,611 A | 4/1990 | Shyu et al. | |
| 5,091,652 A | 2/1992 | Mathies et al. | |
| 5,211,805 A | 5/1993 | Srinivasan | |
| 5,260,578 A | 11/1993 | Bliton et al. | |
| 5,296,700 A | 3/1994 | Kumagai | |

(Continued)

FOREIGN PATENT DOCUMENTS

EP 0050159 4/1981

(Continued)

OTHER PUBLICATIONS

Qingbo et al. "Fully Automated Multiplexed Capillary Systems for DNA Sample Analysis" Sequencing Abstracts—DOE Human Genome Program- Contractor Workshop VIII, Feb. 27-Mar. 2, 2000, Santa Fe, N.M.

(Continued)

*Primary Examiner*—B J Forman

(57) ABSTRACT

Methods and devices for producing a nucleic acid arrays using in situ nucleic acid array synthesis protocols are provided. A feature of certain embodiments of the invention is that control probes are produced in collections of features, e.g., columns, of the arrays that have been selected according to a particular efficient control probe feature/column selection protocol. A feature of certain other embodiments of the invention is that an "all-bases-all-layers" probe set is produced in at least one of column of the arrays. Also provided are devices configured for use in the subject methods, as well as arrays produced using the subject methods and devices as well as methods for using such arrays.

14 Claims, 4 Drawing Sheets

Nozzle/Column (22K Array)

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1 | | | | | | | | 8 | | | | | | | 15 | | | | | |
| | | 22 | | | | | | | 29 | | | | | | | 36 | | | | |
| | | | 43 | | | | | | | 50 | | | | | | | 57 | | | |
| | | | | 64 | | | | | | | 71 | | | | | | | 78 | | |
| | | | | | 85 | | | | | | | 92 | | | | | | | 99 | |
| | | | | | | 106 | | | | | | | 113 | | | | | | | 120 |
| | | | | | | | 127 | | | | | | | 134 | | | | | | |
| 141 | | | | | | | | 148 | | | | | | | 155 | | | | | |
| | 162 | | | | | | | | 169 | | | | | | | 176 | | | | |
| | | 183 | | | | | | | | 190 | | | | | | | 197 | | | |
| | | | 204 | | | | | | | | | | | | | | | | | |

U.S. PATENT DOCUMENTS

| | | | |
|---|---|---|---|
| 5,324,633 A | | 6/1994 | Fodor et al. |
| 5,464,960 A | | 11/1995 | Hall et al. |
| 5,474,796 A | * | 12/1995 | Brennan .................... 427/2.13 |
| 5,585,639 A | | 12/1996 | Dorsel et al. |
| 5,631,734 A | | 5/1997 | Stern et al. |
| 5,760,951 A | | 6/1998 | Dixon et al. |
| 5,763,870 A | | 6/1998 | Sadler et al. |
| 5,772,656 A | | 6/1998 | Klopotek |
| 5,981,956 A | | 11/1999 | Stern |
| 6,078,390 A | | 6/2000 | Bengtsson |
| 6,084,991 A | | 7/2000 | Sampas |
| 6,222,664 B1 | | 4/2001 | Dorsel |
| 6,228,659 B1 | * | 5/2001 | Kowallis et al. ............. 436/180 |
| 6,259,524 B1 | | 7/2001 | Hofstraat et al. |
| 6,284,465 B1 | | 9/2001 | Wolber |
| 6,310,640 B1 | * | 10/2001 | Askeland .................... 347/41 |
| 6,320,196 B1 | | 11/2001 | Dorsel et al. |
| 6,335,934 B1 | | 1/2002 | Sakurai et al. |
| 6,371,370 B2 | | 4/2002 | Sadler et al. |
| 6,406,849 B1 | | 6/2002 | Dorsel et al. |
| 6,420,180 B1 | | 7/2002 | Bass |

FOREIGN PATENT DOCUMENTS

| | | | |
|---|---|---|---|
| EP | | 0557719 | 1/1993 |
| EP | | 0955085 | 10/1999 |
| EP | | 1254704 | 11/2002 |
| EP | | 0918432 | 6/2004 |
| WO | | WO 98/30883 * | 7/1998 |
| WO | | WO9849537 | 11/1998 |
| WO | | WO0159503 | 2/2001 |

OTHER PUBLICATIONS

Agilent G2565AA "Microarray Scanner System" with SureScan Technology—User Manuel, Second Edition, May 2002.

EP Search Report Mailed May 6, 2005.

* cited by examiner

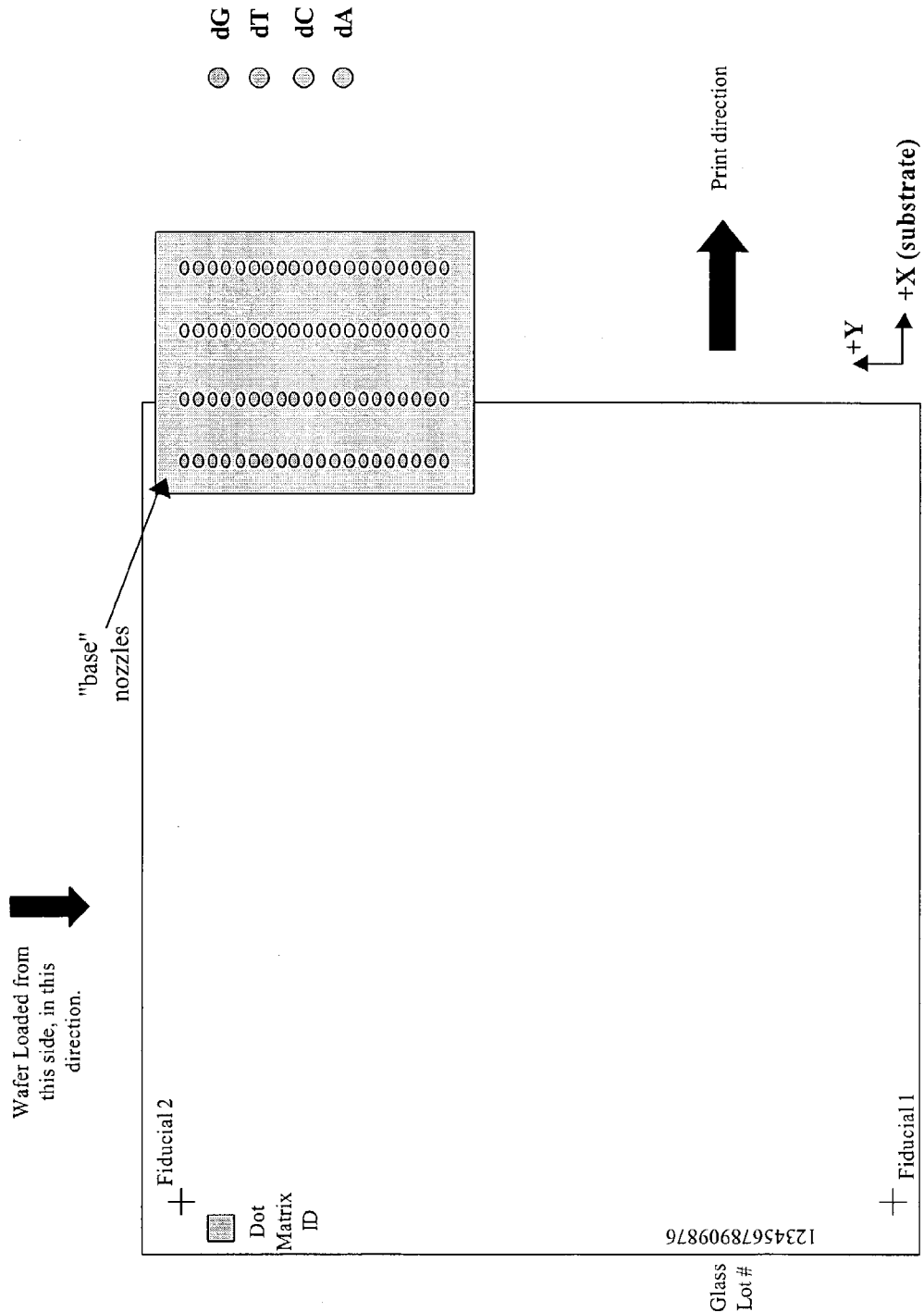

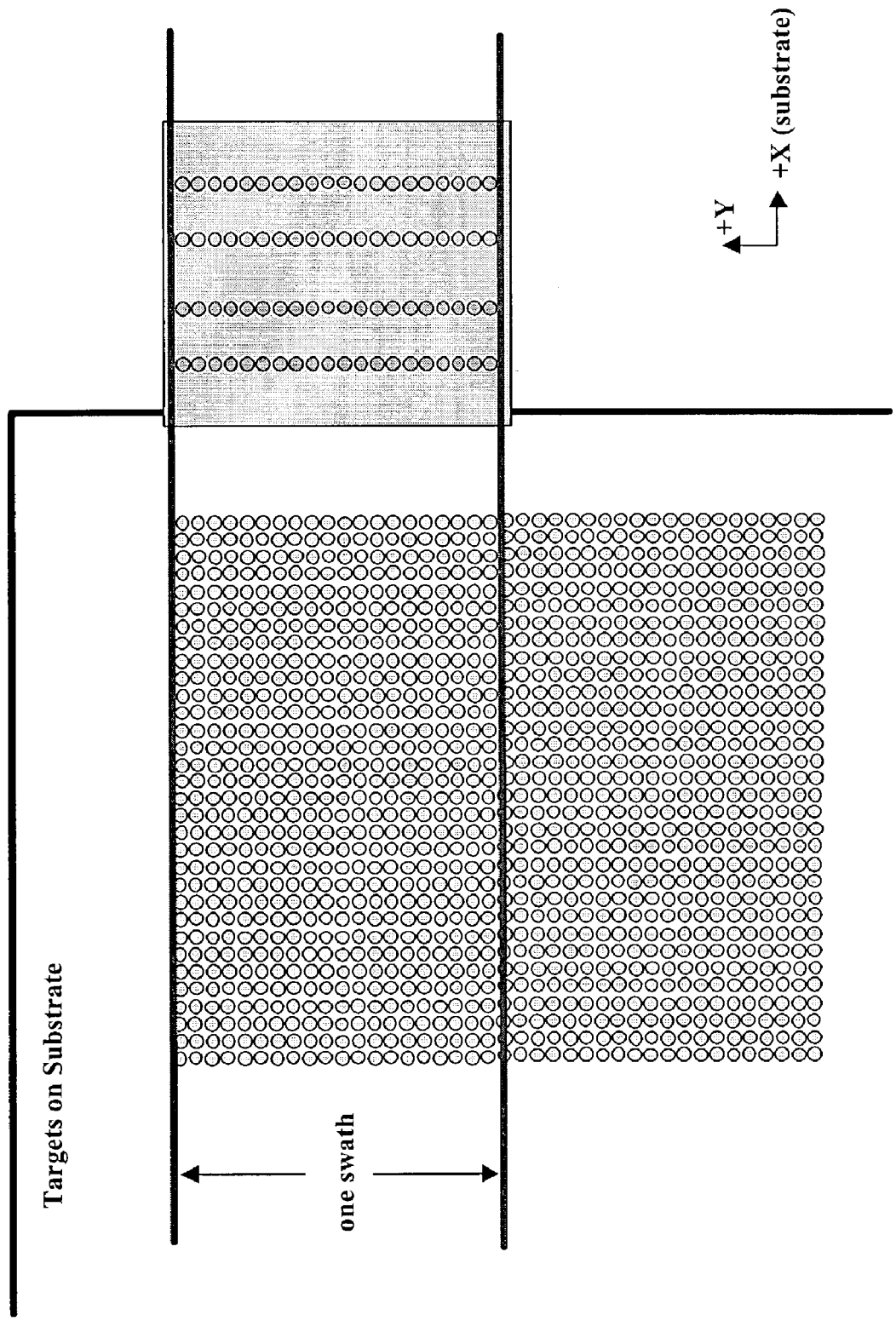

Figure 3

| Nozzle/Column (22K Array) | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |
| 1 | | | | | | | | | | | | | | | | | | | |
| | 22 | | | | | | | | | | | | | | | | | | |
| | | 43 | | | | | | | | | | | | | | | | | |
| | | | 64 | | | | | | | | | | | | | | | | |
| | | | | 85 | | | | | | | | | | | | | | | |
| | | | | | 106 | | | | | | | | | | | | | | |
| | | | | | | 127 | | | | | | | | | | | | | |
| | | | | | | | 148 | | | | | | | | | | | | |
| | | | | | | | | 169 | | | | | | | | | | | |
| | | | | | | | | | 190 | | | | | | | | | | |
| | | | | | | | 8 | | | | | | | | | | | | |
| | | | | 29 | | | | | | | | | | | | | | | |
| | | | | | | | | | 50 | | | | | | | | | | |
| | | | | | | | | | | 71 | | | | | | | | | |
| | | | | | | | | | | | 92 | | | | | | | | |
| | | | | | | | | | | | | 113 | | | | | | | |
| | | | | | | | | | | | | | 134 | | | | | | |
| | | | | | | | | | | | | | | 155 | | | | | |
| | | | | | | | | | | | | | | | 176 | | | | |
| | | | | | | | | | | | | | | | | 197 | | | |
| | | | | | | | | | | | | | | 15 | | | | | |
| | | | | | | | | | | | | | | | 36 | | | | |
| | | | | | | | | | | | | | | | | 57 | | | |
| | | | | | | | | | | | | | | | | | 78 | | |
| | | | | | | | | | | | | | | | | | | 99 | |
| | | | | | | | | | | | | | | | | | | | 120 |
| 141 | 162 | 183 | 204 | | | | | | | | | | | | | | | | |

NUCLEIC ACID ARRAY IN SITU FABRICATION METHODS AND ARRAYS PRODUCED USING THE SAME

FIELD OF THE INVENTION

The present invention relates to biopolymeric arrays, particularly in situ produced nucleic acid arrays.

BACKGROUND OF THE INVENTION

Array assays between surface bound binding agents or probes and target molecules in solution may be used to detect the presence of particular biopolymeric analytes in the solution. The surface-bound probes may be oligonucleotides, peptides, polypeptides, proteins, antibodies or other molecules capable of binding with target biomolecules in the solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing target molecules ("targets") that bind with the attached probes is placed in contact with the bound probes under conditions sufficient to promote binding of targets in the solution to the complementary probes on the substrate to form a binding complex that is bound to the surface of the substrate. The pattern of binding by target molecules to probe features or spots on the substrate produces a pattern, i.e., a binding complex pattern, on the surface of the substrate which is detected. This detection of binding complexes provides desired information about the target biomolecules in the solution.

The binding complexes may be detected by reading or scanning the array with, for example, optical means, although other methods may also be used, as appropriate for the particular assay. For example, laser light may be used to excite fluorescent labels attached to the targets, generating a signal only in those spots on the array that have a labeled target molecule bound to a probe molecule. This pattern may then be digitally scanned for computer analysis. Such patterns can be used to generate data for biological assays such as the identification of drug targets, single-nucleotide polymorphism mapping, monitoring samples from patients to track their response to treatment, assessing the efficacy of new treatments, etc.

Biopolymer arrays can be fabricated using either deposition of the previously obtained biopolymers or in situ synthesis methods. The deposition methods basically involve depositing biopolymers at predetermined locations on a substrate which are suitably activated such that the biopolymers can link thereto. Biopolymers of different sequence may be deposited at difference regions on the substrate to yield the completed array. Typical procedures known in the art for deposition of previously obtained polynucleotides, particularly DNA, such as whole oligomers or cDNA, are to load a small volume of DNA in solution in one or more drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into a drop dispenser in the form of a pulse jet head and fired onto the substrate. Such a technique has been described in WO 95/25116 and WO 98/41531, and elsewhere.

The in situ synthesis methods include those described in U.S. Pat. No. 5,449,754 for synthesizing peptide arrays, as well as WO 98/41531 and the references cited therein for synthesizing polynucleotides (specifically, DNA) using phosphoramidite or other chemistry. Additional patents describing in situ nucleic acid array synthesis protocols and devices include U.S. Pat. Nos. 6,451,998; 6,446,682; 6,440,669; 6,420,180; 6,372,483; 6,323,043; and 6,242,266; the disclosures of which patents are herein incorporated by reference.

Such in situ synthesis methods can be basically regarded as iterating the sequence of depositing droplets of: (a) a protected monomer onto predetermined locations on a substrate to link with either a suitably activated substrate surface (or with previously deposited deprotected monomer); (b) deprotecting the deposited monomer so that it can react with a subsequently deposited protected monomer; and (c) depositing another protected monomer for linking. Different monomers may be deposited at different regions on the substrate during any one cycle so that the different regions of the completed array will carry the different biopolymer sequences as desired in the completed array. One or more intermediate further steps may be required in each iteration, such as oxidation and washing steps.

With respect to in situ preparation of nucleic acid arrays, in many currently employed protocols successive layers are built up, 3' to 5', by pulse-jet depositing an appropriate nucleotide phosphoramidite and an activator to each array feature location of a substrate surface, e.g., a glass wafer surface. The substrate is then removed to a flow cell, and the other phosphoramidite cycle steps (oxidation and deprotection of the 5'-hydroxyl group) are performed in parallel. The substrate is then re-registered, and the next layer is printed.

One exemplary in situ nucleic acid array synthesis device and method for its use is shown in FIG. 1. The printing process is shown diagrammatically in FIGS. 1A and 1B. A detailed view of the printhead is shown in FIG. 2. FIG. 1A shows the relationship between the printing head and the wafer (in this case, a 6" square, capable of yielding 12 1"×3" slides). In what follows, the stage X direction is referred to as "columns" and the direction orthogonal to the stage X direction is referred to as "rows". During printing, the inkjet is stationary, and a stepping stage moves the wafer over the head in the X direction. As the wafer passes over the head, it prints the appropriate phosphoramidite (dG, dT, dC or dA; see FIG. 2) to each feature. Since there are 20 nozzles dispensing each chemical component (numbered 1 through 20 in FIG. 2), the array is printed 20 columns at a time, and each column can be mapped back to a particular nozzle in each well (see FIG. 2). Thus, each column on the final array is associated with a nozzle group with 4 members. The nozzle groups have a periodicity of 20, i.e. columns 1, 21, 41, 61, etc. are all written by the same nozzle group.

Nucleic acid microarrays present a unique challenge to Quality Control (QC) professionals. Microarrays conduct thousands to tens of thousands of quantitative measurements in parallel. However, absolute standard samples exist for few or none of these measurements, and there is as of yet no organization that is seriously attempting to develop such standards. To date, microarray manufacturers have approached this problem in two ways:

1. Representative QC: Manufacturing campaigns include a certain percentage of arrays of a fixed design that are specifically used for QC purposes only. Following hybridization to a specified sample, via a specified protocol, this Representative QC array must then produce data that meet certain pre-determined quantitative standards.

2. Embedded QC: Every array, regardless of design, includes a specific subset of probes that sample the array landscape (i.e. QC probes are "embedded" in each design). These probes must produce data that meet certain quantitative standards, after hybridization to a specified sample, via a specified protocol. Furthermore, in order to provide metrics of data quality during customer use, QC sample(s) targeted to these probes may potentially be included in customer samples.

Representative QC can be used with either custom array designs (i.e. manufacturing campaigns may contain arrays with a variety of relatively uncharacterized designs) or catalog array designs (i.e. manufacturing campaigns contain arrays of only one well-characterized design). Since the Representative QC design is independent of Custom or Catalog array designs, it can be used to assess the quality of production runs of custom designs or catalog array designs and hybridized independently under optimized conditions.

Embedded QC, however, works best with catalog arrays (unless custom array designs are required to contain the embedded grid as well). The advantage of using embedded QC is that it is more efficient and robust, since any array can be sampled for QC purposes. Also embedded QC data can be collected at the point of use or from a pre-release sample, whereas representative QC is always performed before release to the end user. Therefore, embedded QC results will be more representative of the quality of the product since any degradation that occurred after the product was released to the end user (shipping, storage, handling, etc.) will be detectable. However, the disadvantage compared to Representative QC is that it is limited to a fixed budget of features on the array that can be employed for QC purposes. Therefore, it is incumbent upon the Embedded QC designer, to be fastidious, and where possible, assign multiple Embedded QC tasks for a fixed number of probes.

An important function of QC is to sample the performance of each nozzle group, in a relatively uniform manner. One approach to realizing this goal has included the use of "gridline control probes", which are constructed by synthesizing a set of control 25-mer oligonucleotide probes, either directly on the array surface, on top of (i.e. 5' of) a 20-mer oligonucleotide tether, or on top of (i.e. 5' of) a 35-mer oligonucleotide tether. These probes, when exposed to their common complementary labeled 25-mer target in solution, sample all layers of oligonucleotide synthesis on a 60-mer in situ oligonucleotide microarray. Layers 1-20, 26-35 and 46-60 are sampled once, while layers 21-25 and 36-45 may be sampled twice, due to probe overlaps, if the overlapping probes utilize different bases at that layer.

Such gridline probes have found extensive use in Representative QC array fabrication protocols. However, these probes have two disadvantages:

1. In order to sample all of the inkjet nozzles involved in printing an array, the present gridline probes are laid out in continuous rows on the Representative QC array. In order to obtain good sampling of the array surface, many such rows are laid out. The net result is that the gridline probes use up over 60% of the available array features.
2. The single 25-mer control probe sequence shared by the gridline probes samples only 1-2 bases per layer (1 base in regions of no overlap, 2 bases when a layer is sampled by 2 probes that overlap at that layer and utilize a different base at that layer). If printing for an unsampled base fails, the failure is invisible to the gridline probes.

In in situ nucleic acid array synthesis protocols, there is an interest in the development of an Embedded QC probe design approach and layout scheme that enables highly efficient sampling of the work product of several aspects of the in situ nucleic acid array printing process. Of particular interest would be the development of such an approach that enabled the efficient detection of several known array manufacturing error modes via a relatively small number of probes. The present invention satisfies this need.

SUMMARY OF THE INVENTION

Methods and devices for producing nucleic acid arrays using in situ nucleic acid array synthesis protocols are provided. A feature of certain embodiments of the invention is that control probes are produced in collections of features, e.g., columns, of the arrays that have been selected according to a particular efficient control probe feature/column selection protocol. A feature of certain other embodiments of the invention is that an "all-bases-all-layers" probe set is produced in at least one column of the arrays. Also provided are devices configured for use in the subject methods, as well as arrays produced using the subject methods and devices as well as methods for using such arrays.

BRIEF DESCRIPTION OF THE DRAWINGS

FIGS. 1A, 1B and 2 provide a schematic view of a representative pulse-jet in situ nucleic acid array fabrication device and print-head element thereof, respectively.

FIG. 3 provides a table showing a representative collection of control probe columns of a nucleic acid microarray, according to the subject invention.

DEFINITIONS

Figure 2:
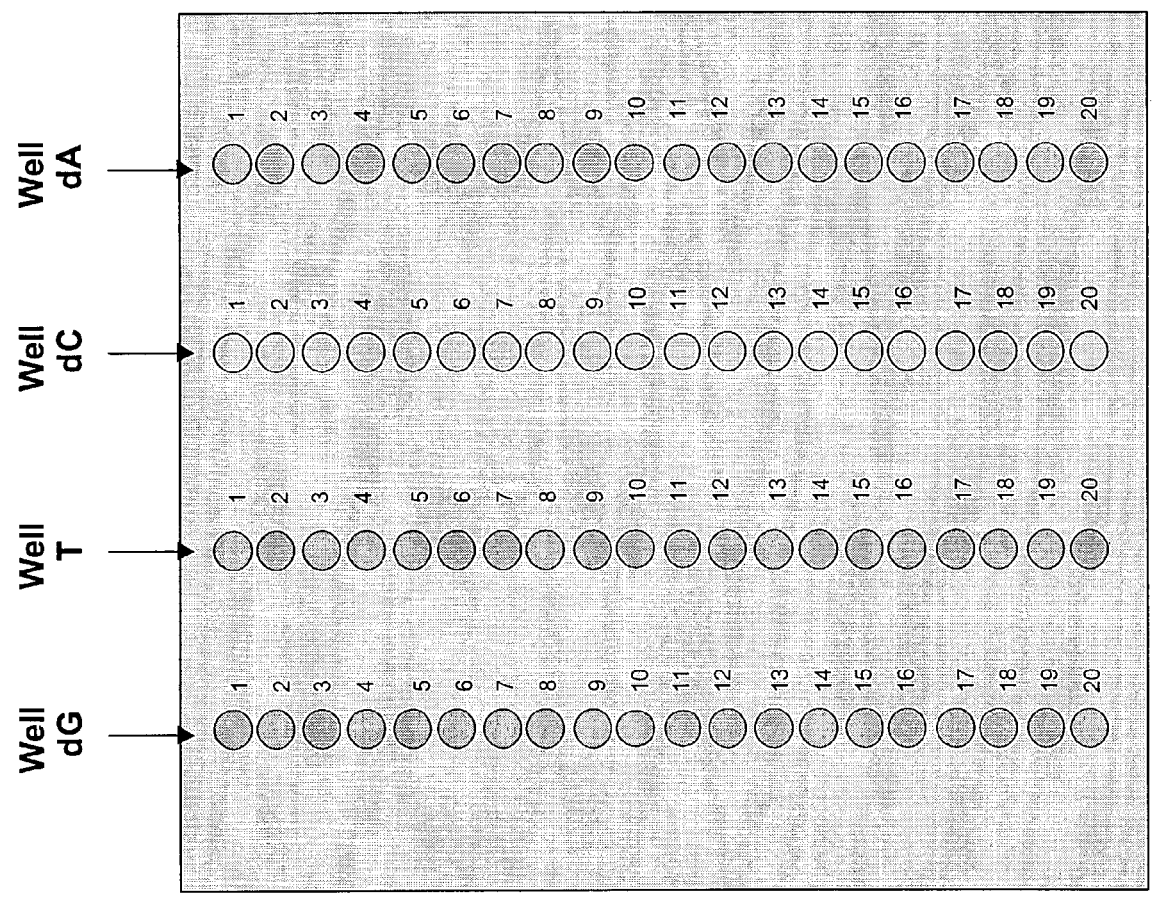

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any one-dimensional, two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 $cm^2$ or even less than 10 $cm^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations.

Each array may cover an area of less than 100 $cm^2$, or even less than 50 $cm^2$, 10 $cm^2$ or 1 $cm^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein. Also, instead of drop deposition methods, light directed fabrication methods may be used, as are known in the art. Interfeature areas need not be present particularly when the arrays are made by light directed synthesis protocols.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The term "substrate" as used herein refers to a surface upon which marker molecules or probes, e.g., an array, may be adhered. Glass slides are the most common substrate for biochips, although fused silica, silicon, plastic and other materials are also suitable.

The term "flexible" is used herein to refer to a structure, e.g., a bottom surface or a cover, that is capable of being bent, folded or similarly manipulated without breakage. For example, a cover is flexible if it is capable of being peeled away from the bottom surface without breakage.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

The substrate may be flexible (such as a flexible web). When the substrate is flexible, it may be of various lengths including at least 1 m, at least 2 m, or at least 5 m (or even at least 10 m).

The term "rigid" is used herein to refer to a structure e.g., a bottom surface or a cover that does not readily bend without breakage, i.e., the structure is not flexible.

The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 60° C. or higher and 3×SSC (450 mM sodium chloride/45 mM sodium citrate). Another example of stringent hybridization conditions is incubation at 42° C. in a solution containing 30% formamide, 1M NaCl, 0.5% sodium sarcosine, 50 mM MES, pH 6.5. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

Methods and devices for producing nucleic acid arrays using in situ nucleic acid array synthesis protocols are provided. A feature of certain embodiments of the invention is that control probes are produced in collections of features, e.g., columns, of the arrays that have been selected according to a particular efficient control probe feature/column selection protocol. A feature of certain other embodiments of the invention is that an "all-bases-all-layers" probe set is produced in at least one of column of the arrays. Also provided are devices configured for use in the subject methods, as well as arrays produced using the subject methods and devices as well as methods for using such arrays.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein. Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing the invention in greater detail than provided in the Summary and as informed by the Background and Definitions provided above, representative embodiments of the subject efficient control probe column selection protocols are described first in greater detail, followed by a review of the subject "all-bases-all-layers" control probe sets of the subject invention. Also provided are discussions of representative applications in arrays featuring the above inventive features find use.

Efficient Selection of Control Probe Features/Columns

As summarized above, the subject invention provides methods for selecting a collection of features in a nucleic acid array in which to locate or place control probes during in situ synthesis of the array, where an array having embedded control probes (an embedded QC array) is produced. In other words, the subject invention provides methods for determining or identifying features (as well as collections thereof, e.g., columns in two-dimensional or three-dimensional arrays) in a nucleic acid microarray in which to produce control probes. Put another way, the subject invention provides methods of selecting a collection of features of a nucleic acid microarray in which to produce control probes, and specifically embedded control probes.

A feature of the subject methods is that one first identifies a set of feature locations that samples all of the nozzle groups Y of a pulsejet head device that is to be employed in making the array. As such, the identified set of features is one that includes probes produced from every nozzle group of the pulse jet head of the in situ synthesis device. In addition, the selected or identified features are ones that are located in all regions of the array that is to be produced, i.e., that are located across the entire surface of the array, such that there are no regions of the array that lack control probes. Features are considered to be located in all regions of the array if any region of the array that is 25%, such as 15% or 10%, including 5%, 4%, 3%, 2% etc., of the total area of the array occupied by features includes a control probe feature. In certain embodiments, the identified features in this step make up less than about 60% of the total number of features of the array, such as less than about 50%, including less than about 40%, less than about 30%, less than about 25%, less than about 20% etc., of the total number of features of array.

In certain embodiments, the set of features that are selected is a set of features that samples less than all of the nozzle groups in a given swath of a given pass but samples all of the nozzle groups in the total number of swaths of a given pass. As illustrated in FIG. 1B, the reagent deposition printing protocol can be viewed as being performed in a number of passes, depending on the length of the probes to be produced, where each pass is made up of a number of swaths. For example, a protocol for printing 25-mer probes may be made up of 25 distinct passes. Depending upon the size of the array, each given pass may be made up of 10 swaths, for example. In this illustrative scenario, the set of features that is chosen for use as control probe features will be ones that sample less than all of the nozzle groups in any given swath, e.g., less than 90%, less than 80%, less than 70%, less than 60%, less than 50%, less than 40%, less than 30%, less than 25%, less than 20%, less than 15%, less than 10% or fewer (in terms of number %). However, in the total number of swaths Z (e.g., 10 in this embodiments) that make up each pass, each of the nozzel groups is sampled at least once. Within any given swath, that portion or fraction of the total number of nozzle groups that is sampled may be sampled one or more times, e.g., up to 5 or more times, including 2, 3, and 4 or more times. Typically, the same set of features is employed as control probe feature locations in each pass.

Following identification of a set of features as described above, one then selects the identified set of feature locations as the collection of feature locations of the microarray in which to produce control probes.

As mentioned above, in certain embodiments the collection of feature locations is a collection of columns of feature locations, as described in greater detail in the embodiment below. In certain embodiments, the selected set of feature locations make up a regular pattern, such that a pattern of repeating periodicity is selected, as described below. In yet other embodiments, the set of feature locations make up a random pattern, where the pattern lacks any defined periodicity.

A feature of certain embodiments of the control probe feature selection process is that it is a "control probe column" selection process, where a feature of these embodiments of the subject invention is that they provide for an efficient sampling of the surface of the array on which the nucleic acid probes are synthesized. As such, the subject methods of these embodiments can also be referred to as "efficient control probe column" selection processes.

In these embodiments, the subject invention provides methods for selecting columns in a nucleic acid array in which to locate or place control probes during in situ synthesis of the array, where an array having embedded control probes (an embedded QC array) is produced. In other words, the subject invention provides methods for determining or identifying columns in a nucleic acid microarray in which to produce control probes. Put another way, the subject invention provides methods of selecting a collection of columns of a nucleic acid microarray in which to produce control probes, and specifically embedded control probes. A feature of the "control probe column" selection process of the subject invention is that it provides for an efficient sampling of the surface of the array on which the nucleic acid probes are synthesized. As such, the subject methods can also be referred to as "efficient control probe column" selection processes.

The subject control probe column selection protocols are designed for use with pulse-jet in situ nucleic acid array synthesis protocols and devices. Patents describing representative pulse-jet in situ nucleic acid array synthesis protocols and devices include, but are not limited to: U.S. Pat. Nos. 6,451,998; 6,446,682; 6,440,669; 6,420,180; 6,372,483; 6,323,043; and 6,242,266; the disclosures of which patents are herein incorporated by reference.

In such protocols, a device that includes a printhead with a plurality of nozzle groups is typically employed. In many such devices, the number of nozzle groups typically ranges from about 5 to about 512, usually from about 10 to about 256, such as from about 5 to about 50, e.g., 20.

In practicing the subject methods, one first determines the total number nozzle groups (hereinafter referred to as Y) in the in situ nucleic acid array synthesis device that will be employed. One then determines the total of columns (hereinafter referred to as X) that are to be produced on the array. In many embodiments, the total number of columns that are produced ranges from about 45 to about 500, such as from about 50 to about 500, including from about 90 to about 275.

Knowing both Y and X, one then identifies a pattern period in which to produce control probes. More specifically, one then identifies or determines a periodicity of columns in which to print control probes. Put another way, one identifies how many columns in a given row that are to have no control probes are to be produced between columns that are to include control probes.

The pattern periodicity (sometimes referred to herein as Z) that is identified with the subject methods is one that either: (i) shares no prime factors with Y and when multiplied by Y produces a product that does not exceed X; or (ii) shares a single prime factor of 2 with Y and when multiplied by Y produces a product that does not exceed X.

Thus, in certain embodiments, the identified or chosen periodicity pattern Z (i.e. periodicity of control probe columns in a given row of columns) is an integer that shares no prime factors with Y and, when multiplied by Y, does not exceed X. In these embodiments, because the pattern is periodic on a given row, the overall pattern of columns in which control probes are produced is one that samples all nozzle groups of the printhead once before returning to the nozzle group that started the pattern.

A representative example of a control probe column selection protocol according to the subject methods is now provided for a device that has 20 nozzle groups in the printhead. FIG. 3 shows the results of sampling one row of a 215 column×105 row microarray, with a period of 7 columns. The numbers at the top of the table enumerate the nozzle groups, while the numbers inside the table designate the column on the array that is sampled. The sampling pattern wraps around every 20 columns (since there are 20 nozzle groups). It is clear from FIG. 3 that by the time the pattern reaches column 134 (the greatest array column number ≦7×20=140), every nozzle group has been sampled once. At column 141 (the smallest column number ≧7×20=140), the sampling pattern begins to repeat. By the first specific protocol described above (i.e., period pattern on a given row; Z shares no prime factors with Y and Z×Y is less than X), spacings of 3 columns and 9 columns (in addition to the above exemplified 7 column period or spacing) would also work, since 3 is prime and is not a factor of 20, while 9=$3^2$ shares no prime factors with 20=5× $2^2$. However, 8 (=$2^3$) will not work, since it shares 2 factors of 2 with 20, while 11 will not work, even though it is prime and not a factor of 20, because 11×20=220>215 (i.e. the pattern will run out of columns on the array before sampling all nozzle groups).

Following identification of the control column pattern period Z, the identified pattern period Z is then used to select or choose a collection or plurality of columns of the to be produced microarray in which to produce control probes. Specifically, the pattern period is used to determine those columns of the to be produced microarray in which to produce control probes during the in situ nucleic acid array synthesis. For example, where a pattern period of 7 is chosen, as described above, one then uses in the pattern period to determine the columns of the array (collectively referred to as a column pattern) in which to print the control probes, e.g., by starting with the first column and printing control probes from nozzle group 1 in that column, then moving over 7 columns to reach column 8, and printing control probes from a second nozzle group, e.g., nozzle group 8, in column 8, and so forth.

In certain embodiments, the pattern of control probe columns starts with the first column in a given array. A representative example of this configuration or embodiment is shown in the table of FIG. 3. However, the pattern shown in FIG. 3 does not sample all nozzle groups equally (groups 5-7, 11-14 and 18-20 are sampled once, while the rest are sampled twice). If several rows of this pattern are distributed across an array, the resulting sample is bimodal: N rows would yield N or 2N samples, depending upon the nozzle group. In certain embodiments, such a result is undesirable from a statistical point of view.

As such, in certain embodiments, an initial column in which to print control probes is selected that results in control probes being printed in substantially the same number of replicate columns per nozzle group. By substantially the same number of replicate columns per nozzle group is meant that any variation in the total number of columns selected for any two nozzle groups does not vary by more than about 4, such as by not more than about 3, including by not more than about 2, by not more than about 1, and in certain embodiments there is no variation. Such a desirable result is also referred to herein as "dithering." Dithering has the effect of cyclically permuting the order in which the nozzle groups are sampled. This permutation, in turn, changes which nozzle groups are sampled twice. Where desired, dithering can be used to produce overall patterns that efficiently sample the entire array surface and all nozzle groups, with about the same number of replicates per nozzle group. In certain representative embodiments, the starting or initial column in which control probes are produced is 1+N, wherein N is an integer ranging from 1 to Z As indicated above, in certain embodiments the chosen or selected pattern periodicity Z is one that shares a single prime factor of 2 with Y and when multiplied by Y produces a product that does not exceed X. In other words, Z is a pattern period that is periodic in a given row and shares a single prime factor of 2 with Y, where Z×Y does not exceed X. Such an approach to selection of a control probe column pattern is particularly desired in methods that are further characterized by selecting a first collection of columns in which to print control probes and then a second collection of columns in which to print control probes, wherein the second collection of columns has an initial column that is adjacent to the initial column of said first collection of columns. For example, where two collections of control probe columns are identified to be used together, the first column of the first control pattern is N and the first column of the second control probe column pattern is N+1. The combination of the two patterns efficiently samples all nozzle groups of a given printhead.

A representative control probe column pattern selection protocol or method according to the subject invention is described in greater detail in the experimental section, below.

The above protocol or method allows one to select a control probe column pattern that efficiently samples the nozzle groups of a printhead of a device across an entire surface of an array substrate.

Once a pattern is identified, a nucleic acid array is synthesized using in situ protocols, where control probes are produced in the control probe columns of the identified patterns. The number of distinct features of a given control probe column that are control probes, as opposed to test probes, may vary, but typically ranges from about 1% to about 10%, where representative ranges include from about 1% to about 5%, including from about 1% to about 3%.

Any convenient control probes can be produced in the identified control probe features/columns of the pattern, where in certain embodiments of interest, the "all-bases-all-layers" control probes of the subject invention described in greater detail below are of produced in the identified control probe columns.

Programming for practicing at least certain embodiments of the above-described methods is also provided. For example, algorithms that are capable of determining a control probe column pattern from input values of X and Y are provided. Programming according to the present invention can be recorded on computer readable media, e.g., any medium that can be read and accessed directly or indirectly by a computer. Such media include, but are not limited to: magnetic tape; optical storage such as CD-ROM and DVD; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above-described methodology.

In certain embodiments, the system is further characterized in that it provides a user interface, where the user interface presents to a user the option of selecting among one or more different, including multiple different, inputs, e.g., of X and Y, dithering parameters, pattern period selection algorithm, etc.

Also provided by the subject invention are in situ pulse-jet nucleic acid array printing devices that include programming that directs the devices to print control probes in a control probe column pattern as identified according to the subject methods. A variety of known and to be developed in situ pulse jet array fabrication devices can be adapted as described above, where representative pulse-jet devices include, but are not limited to, those described in U.S. Pat. Nos. 6,451,998; 6,446,682; 6,440,669; 6,420,180; 6,372,483; 6,323,043; and 6,242,266; the disclosures of which patents are herein incorporated by reference.

Also provided are methods of using such devices to produce nucleic acid arrays, where such methods include the steps of identifying a pattern of control probe columns according to the subject invention and then producing the array via in situ protocols, where control probes are produced in the control probe columns of the identified pattern. Any in situ pulse jet array fabrication protocols or methods can be adapted as described above, where representative in situ fabrication protocols include, but are not limited to, those described in U.S. Pat. Nos. 6,451,998; 6,446,682; 6,440,669; 6,420,180; 6,372,483; 6,323,043; and 6,242,266; the disclosures of which patents are herein incorporated by reference.

Arrays produced by the above-described methods are characterized by having control probes printed in the collections of feature, e.g., columns of the control probe column pattern, which are identified by the subject methods and described above the above provided formulas. The actual control probes produced in the identified control probe features and columns thereof may be any convenient control probes, including both positive and negative control probes, where a variety of such control probes are known to those of skill in the art. Of particular interest in certain embodiments are "all-bases-all-layers" control probe collections, as described in greater detail below. Such arrays find use in a variety of applications, as described in greater detail below.

Utility

The above-described control probe feature/column identification methods and devices programmed to practice the same may be used to deposit nucleic acids on surfaces of any of a variety of different substrates, including both flexible and rigid substrates, e.g., in the production of nucleic acid arrays. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example, a slide or plate configuration, such as a rectangular or square disc. In many embodiments, the substrate will be shaped generally as a rectangular solid, having a length in the range of about 4 mm to 200 mm, usually about 4 mm to 150 mm, more usually about 4 mm to 125 mm; a width in the range of about 4 mm to 200 mm, usually about 4 mm to 120 mm, and more usually about 4 mm to about 80 mm; and a thickness in the range of about 0.01 mm to about 5 mm, usually from about 0.1 mm to about 2 mm and more usually from about 0.2 mm to about 1 mm. However, larger or smaller substrates may be and can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fuse silica; silicon, plastics (for example polytetraflouroethylene, polypropylene, polystyrene, polycarbonate, and blends thereof, and the like); metals (for example, gold, platinum, and the like). The substrate surface onto which the polynucleotide compositions or other moieties are deposited may be smooth or substantially planar, or have irregularities, such as depressions or elevations. The surface may be modified with one or more different layers of compounds that serve to modify the properties of the surface in a desirable manner. Such modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyetheyleneamines, polyarylene sulfides, polysiloxanes, polyimides, polyacetates, and the like, where the polymers may be hetero- or homopolymeric, and may or may not have separate functional moieties attached thereto (for example, conjugated).

All-Bases-All-Layers Control Probes

As summarized above, the subject invention also provides collections of probes referred to herein as "all-bases-all-layers" control probes, which collections are collections of nucleic acid probes that collectively include a base residue that has been deposited by every nozzle member of a given nozzle group at every layer or position in a given control probe. In other words, the subject invention provides "all-bases-all-layers" collections of control probes that are made up of a plurality of different probes of different sequence which, collectively, have a base or residue deposited by every nozzle of a given nozzle group at every layer. As such, the subject collections of "all-bases-all-layers" control probes ensure that for a given nozzle group, every nozzle of that group is sampled or represented in the control probes at every layer.

A given collection of "all-bases-all-layers" control probes may be made up of a single set of control probes or a plurality of different sets of control probes, depending on the length of test probes in a given array for which the collection of control probes is to serve as a control and the nature of the particular control probes that make up a given set. Thus, in certain embodiments, a collection of "all-bases-all-layers" control probes according to the subject invention may be made up of a single set of control probes. In yet other embodiments, a collection of "all-bases-all-layers" control probes according to the subject invention may be made up of a plurality of different sets of control probes, where plurality means at least 2, wherein in many embodiments, the number of sets of less than 4, for example less than 4, such as 2 or 3.

As mentioned above, whether a given collection of control probes includes one or more sets of control probes depends, at least in part, on the nature of the control probes that make up the control set and the length of the test probes. Where the test probes of the array are the same length as the control probes, only a single set of control probes is present in the collection of control probes in certain embodiments. For example, where the test probes are all 25-mers, only a single set of 25-mer control probes may make up a collection of control probes for use on such an array. In other embodiments where the test probes are longer than the control probes, a given collection of control probes may be made up of two or more sets of control probes, so that the entire length or all layers of the test probes are represented in the control probes. For example, in those embodiments where the surface-bound probes (i.e., test probes) are longer than ~30 bases (i.e., are longer than 30-mers), the difference between the hybridization efficiencies of a target sequence to its complementary probe and to a single base mismatch or deletion derived from that probe can decrease to a level comparable to other sources of chemical noise (most notably, the chemical noise in the hybridization assay used to develop a signal from the probe). Therefore, it is desirable in many embodiments to keep the length of the test targets less than ~30 bases, in order to maintain assay resolution. In such embodiments, it may be desirable to have two or more sets of control probes. For example, where the test probes are 60-mers, three sets or versions of four 25-mer length control probes (one set for layers (residues) 1-25 of the test probes, one set for layers (residues) 21-45 of the test probes and one set for layers (residues) 36-60 of the test probes; 3 sets with a total of 12 probes making up the collection of control probes) would sample all bases at all layers of the test probes. In another embodiment where the use of a minimum number of control probes is desired, a reduced number can be employed by noting that wrong or missing bases near the ends of a 60-mer probe are not as disruptive to hybridization as wrong or missing bases closer to the center of the probe and that the 5 bases closest to the array surface contribute little to the overall hybridization efficiency. In such an embodiment, the number of sets of control probes could be reduced to 2 (8 control probes in the collection) (one set of 4 control probes to sample layers 6-30 and one set of 4 control probes to sample layers 31-55). The number of sets of control probes can also be reduced to 2 sets of four probes by employing 30-mer probes and targets (with some loss of resolution). In yet other embodiments, composite probes having two or more different probe domains that are employed with a corresponding number of sets of distinguishably labeled control targets, e.g., two different distinguishably labeled control target sets for composite probes of two different domains, are employed, where the composite probes are equal in length to the test probes even if the test probes exceed 30 bases in length. Such composite probes and their use are described in greater detail below.

Each set of control probes is made up of four different control probe nucleic acids of differing sequence each having at least a first probe domain of from about 4 to about 30 nucleotide residues, wherein each member probe nucleic acid of the set has a different base from any other member of the set at each residue position of said first probe domain. For example, at position or residue 1 of a given probe domain, control probe 1 of the set may have A, control probe 2 of the set may have G, control probe 3 of the set may have C and control probe 4 of the set may have T. An exemplary set of four 6-mer control probes would be:

```
5'-ATGCTC-surface

5'-CACTGA-surface

5'-TGAGCT-surface

5'-GCTAAG-surface
``` where each probe of the set has a single probe domain of 6 residues long.

As mentioned above, the control probes of a given set of control probes include at least one probe domain of from about 4 to about 30 bases in length, where the length is typically from about 5 to about 30, e.g., about 10 to about 30, about 15 to about 25, etc. In certain embodiments, the control probes that make up a given set include a single probe domain. In yet other embodiments, the control probes include a plurality of two or more probe domains, where the number of different probe domains of such embodiments (where the probes are referred to as composite control probes) may range from 2 to about 10, including 2 to 5, e.g., 2 to 4, such as 2 to 3. As mentioned above, composite probes may be of interest where one wishes to use a collection of control probes made up of a minimum number of control probes to sample all bases at all layers of test probes that are longer than 30 mers, e.g., 45 mers, 60 mers, 75 mers, 90 mers, etc. For example, where the test probes on a given array are 60 mers, one could have a collection of control probes made up of a single set of control probes each being 60 bases long and made up of 2 out of four possible probe domains. For example, consider 4 sequences of length ≦30 (i.e., probe domains) that employ a different base at each position. Designate these sequences A, B, C and D. Then the composite probes 5'-A-B-surface
5'-B-A-surface
5'-C-D-surface
5'-D-C-surface sample every base at every layer. The above collection of composite control probes of two different probe domains are capable of sampling all bases at all layers of 60 mer test probes (where the complementary targets to A and B are labeled with a different moiety measurable independently (similarly for C and D) as described in greater detail below).

In using the collection of control probes, a corresponding set of four labeled control target nucleic acids is employed during use of the array for each probe domain of the control probes in the collection (Actual use of the array in hybridization assays is described in greater detail below). By corresponding is meant that the set of control target nucleic acids includes a target nucleic acid that hybridizes under stringent conditions to a control probe member of the set, where the set of control target nucleic acids includes a target nucleic acid for each member of the control probe set. In many embodiments, the target nucleic acids are perfect complements of the control probes of the sets for which they are designed, meaning that each control probe-control target pair in the union of the control probe and control target sets are perfect complements and hybridize to form duplex molecules with no mismatch basepairs.

Where the control probes of a given collection each include only a single probe domain, all of the control target nucleic acids that are used with the control probes during use of the array may be labeled with a single detectable label. One way of labeling which may find use in the subject invention is isotopic labeling, in which one or more of the nucleotides is labeled with a radioactive label, such as $^{32}S$, $^{32}P$, $^{3}H$, or the like. Another means of labeling is fluorescent labeling in which fluorescently tagged nucleotides, e.g. CTP, are present in the control target nucleic acids. Particular examples of fluorescent labels which may be used under the invention include, but are not limited to: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl] benzoic acid ethyl ester monohydrochloride (R6G)(emits a response radiation in the wavelength that ranges from about 500 to 560 nm), 1, 1, 3, 3, 3', 3'-Hexamethylindodicarbocyanine iodide (HIDC) (emits a response radiation in the wavelength that ranged from about 600 to 660 nm), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like.

Where composite probes are employed, a control target set for each different probe domain of the target probes is employed during use, where each set is distinguishably labeled (i.e., labeled with a different type of label so as to be distinguishable from each other). For example, with the above representative set of four composite probes having probe domains A, B, C and D, two distinguishable labels (designated g (green) and r (red)) are used with corresponding targets a, b, c and d, so that the target combination [g-a, r-b, g-c, r-d] yields distinguishable signals. Any combination of sequences and labels that ensures that the two potential targets of each composite probe bear different labels will yield distinguishable signals.

Where composite probes are employed, the sequences of the probe domains, e.g., A, B, C and D, and their complementary targets of the target sets, e.g., a, b, c and d, typically possess a number of special properties in addition to being different at each position:
1. The target sequences a, b, c and d must hybridize specifically to only their complementary probe. They should not cross-hybridize to any other control or experimental (i.e., test) probe on the array.
2. The composite probes should not possess appreciable secondary structure.
3. The targets should not possess appreciable secondary structure.
4. The melting temperatures of the four probe/target duplexes should be approximately equal.

Where composite probes are employed, any convenient protocol for identifying suitable sequences for each of the composite probe domains (and therefore complementary targets) that satisfy the above parameters may be employed. Generally, if the probe domains are of length L, then there are $4^L$ possibilities for sequence A, $3^L$ possibilities for sequence B (given A), $2^L$ possibilities for sequence C (given A and B) and only one possibility for sequence D (given A, B and C). Two representative approaches to identifying sequences for the various composite probe domains, e.g., A, B, C and D, are:
1. Monte Carlo Method: Generate sequences at random, and screen for the desired properties.
2. Sequential Method: Generate a single sequence A that possesses all the needed single-sequence properties, then use it as a seed to generate sequences B, C and D. The generation method generally preserves the desirable properties of A, but does not produce a family of probes whose targets hybridize efficiently to more than one member of the probe family.

In certain embodiments, the sequential method is more desirable, since it may require less processing steps than the Monte Carlo method. The Sequential Method is further described in the Experimental Section, below.

The above-described collections of "all-bases-all-layers" probes can be employed on any nucleic acid array as embedded QC probes, where the collections of control probes are particularly suited for use with in situ produced nucleic acid arrays, such as the arrays having control probe column patterns selected according to the above described methodology. Arrays that include the above described "all-bases-all-layers" control probe collections and methods for their use, as well as representative applications in which the arrays find use, are now reviewed in greater detail in the following sections.

Arrays

Also provided by the subject invention are novel nucleic acid arrays of produced using the subject methods, as described above. The subject arrays include at least two distinct nucleic acids that differ by monomeric sequence immobilized on e.g., covalently or non-covalently attached to, different and known locations on the substrate surface. Each distinct nucleic acid sequence of the array is typically present as a composition of multiple copies of the polymer on the substrate surface, e.g. as a spot on the surface of the substrate. The number of distinct nucleic acid sequences, and hence spots or similar structures (i.e., array features), present on the array may vary, but is generally at least 2, usually at least 5 and more usually at least 10, where the number of different spots on the array may be as a high as 50, 100, 500, 1000, 10,000 or higher, depending on the intended use of the array. The spots of distinct nucleic acids present on the array surface are generally present as a pattern, where the pattern may be in the form of organized rows and columns of spots, e.g., a grid of spots, across the substrate surface, a series of curvilinear rows across the substrate surface, e.g., a series of concentric circles or semi-circles of spots, and the like. The density of spots present on the array surface may vary, but will generally be at least about 10 and usually at least about 100 spots/cm², where the density may be as high as $10^6$ or higher, but will generally not exceed about $10^5$ spots/cm². In the subject arrays of nucleic acids, the nucleic acids may be covalently attached to the arrays at any point along the nucleic acid chain, but are generally attached at one of their termini, e.g., the 3' or 5' terminus.

A feature of the subject arrays is that they at least include one of: (1) a pattern of control probe columns selected or chosen according to the above described methodology, such that the pattern of control probe columns in the array satisfies the above described rules or parameters employed in the above-described methodology; and (2) a collection of "all-bases-all-layers" control probes, as described above. Thus, in certain embodiments the subject arrays are characterized by having a pattern of control probe columns selected or chosen according to the above described methodology, such that the pattern of control probe columns in the array satisfies the above described. In certain other embodiments, the subject arrays are characterized by including a collection of "all-bases-all-layers" control probes, as described above. In yet other embodiments, the subject arrays are characterized by including both: (1) a pattern of control probe columns selected or chosen according to the above described methodology, such that the pattern of control probe columns in the array satisfies the above described rules or parameters employed in the above-described methodology; and (2) a collection of "all-bases-all-layers" control probes, as described above.

Utility of Arrays

The subject arrays find use in a variety applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g., an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Where the arrays include "all-bases-all-layers" control probes, as described above, a collection of labeled control targets is typically included in the sample, where the collection may be made up of control targets that are all labeled with the same label or two or more sets that are distinguishably labeled with different labels, as described above. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER device available from Agilent Technologies, Palo Alto, Calif. Other suitable apparatus and methods are described in U.S. Pat. Nos. 5,091,652; 5,260,578; 5,296,700; 5,324,633; 5,585,639; 5,760,951; 5,763,870; 6,084,991; 6,222,664; 6,284,465; 6,371,370 6,320,196 and 6,355,934; the disclosures of which are herein incorporated by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

Kits

Kits for use in analyte detection assays are also provided. The kits at least include the arrays of the invention, as described above. Where the arrays include the above described "all-bases-all-layers" control probes, the kits may further include labeled collections of control target nucleic acids made up of targets corresponding to the probe domains of the control probes in the collection of control probes on the array, where the collection of control target nucleic acids may be made up of a targets that are all labeled with the same label or two or more sets of distinguishably labeled target nucleic acids. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the array assay devices for carrying out an array based assay. Such kits also typically include instructions for use in practicing array based assays.

Kits for use in connection with the control probe column selection protocols of the subject invention may also be provided. Such kits preferably include at least a computer readable medium including programming as discussed above and instructions. The instructions may include installation or setup directions. The instructions may include directions for use of the invention.

Providing software and instructions as a kit may serve a number of purposes. The combinations may be packaged and purchased as a means of upgrading an existing fabrication device. Alternatively, the combination may be provided in connection with a new device for fabricating arrays, in which the software may be preloaded on the same. In which case, the instructions will serve as a reference manual (or a part thereof) and the computer readable medium as a backup copy to the preloaded utility.

The instructions of the above described kits are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

The following examples are offered by way of illustration and not by way of limitation.

EXPERIMENTAL

I. Efficient Sampling Pattern Example:

Designate a one row periodic sampling pattern that occupies row R, begins at column C and uses column spacing Z as R-C-Z. For example, a pattern that occupies row 1, begins at column 4 and uses column spacing 7 is designated 1-4-7. Then the combination of 4 rows implied by [1-7-7, 29-5-7, 57-3-7, 84-1-7] samples the nozzle groups of a 215 column× 105 row array as shown in Table 1.

TABLE 1

| Nozzle Group | | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| Samples | 7 | 6 | 7 | 6 | 6 | 6 | 6 | 7 | 6 | 7 | 6 | 6 | 6 | 6 | 7 | 6 | 6 | 5 | 6 | 5 |

The pattern samples all nozzle groups at least 5 times and at most 7 times. In addition, the pattern samples the entire array surface, and is therefore capable of detecting long-range gradients in overall probe synthetic efficiency.

II. Construction of All-Bases-All-Layers Probes:

The Sequential Approach to Composite Probe design is used to construct four sequences that sample all bases in layers 6-55 of a 60-mer array in the example that follows.

For the first probe, pick the existing 25-mer QC probe Pro25G:

5'-ATCATCGTAGCTGGTCAGTGTATCC-3' (Pro25G) (SEQ ID NO:01)

The sequence Pro25G was designed to possess minimal self-structure and a reasonably even base composition (empirical formula $A_5C_6G_6T_8$; 48% GC). It is therefore a good "seed" candidate, since its even base composition ensures the maximum number of possible derived sequences with nearly equivalent duplex melting temperatures. To begin generation of the next probe, cyclically permute Pro25G, starting at G(13) to minimize target overlap:

```
5'-ATCATCGTAGCTGGTCAGTGTATCC-3' (Pro25G)  (SEQ ID NO:01)
              |||--|||-|-
5'-GGTCAGTGTATCCATCATCGTAGCT-3' (BX)      (SEQ ID NO:02)
```

In the sequence listing above, dashes (−) indicate base differences at a given layer, while pipes (|) indicate base identity at that layer. The challenge is to remove the base identities, with minimum disturbance to the base composition (and duplex melting temperature). This can be done via base exchanges in sequence BX. Exchanging T(15) with G(20), C(16) with T(21), A(17) with T(25) and A(21) with C(24) in sequence BX yields sequence EQCP1:

```
5'-ATCATCGTAGCTGGTCAGTGTATCC-3' (Pro25G)  (SEQ ID NO:01)
   -------------------------
5'-GGTCAGTGTATCCAGTTTCTCCGAA-3' (EQCP1)   (SEQ ID NO:03)
```

To begin generation of the third probe, cyclically permute and reverse Pro25G, starting at A(17):

```
5'-ATCATCGTAGCTGGTCAGTGTATCC-3'  (Pro25G)  (SEQ ID NO:01)
   ------------------------
5'-GGTCAGTGTATCCAGTTTCTCCGAA-3'  (EQCP1)   (SEQ ID NO:03)
   X-|----|X--|-|-|X-||--|--
5'-ACTGGTCGATGCTACTACCTATGTG-3'  (CX)      (SEQ ID NO:04)
```

In the sequence listing above, dashes (–) indicate that all 3 bases differ at that layer, pipes (|) indicate base identity between CX and EQCP1 at that layer, and X indicates base identity between Pro25G and CX at that layer. Again, resolve base identities via base exchanges, whenever possible. Exchanging A(1) with T(3), G(8) with A(9), C(12) with A(17), A(14) with T(16) and C(19) with G(23) yields

```
5'-ATCATCGTAGCTGGTCAGTGTATCC-3'  (Pro25G)  (SEQ ID NO:01)
   ------------------------
5'-GGTCAGTGTATCCAGTTTCTCCGAA-3'  (EQCP1)   (SEQ ID NO:03)
   -------------------|-----
5'-TCAGGTCAGTGATTCACCGTATCTG-3'  (CY)      (SEQ ID NO:05)
```

This leaves one uncorrected base identity at T(20) of sequence CY. Since this identity cannot be resolved via an exchange, it must be resolved via a change. In order to maintain the same GC content as Pro25G in the new sequence, T(20) is changed to an A, yielding

```
5'-ATCATCGTAGCTGGTCAGTGTATCC-3'  (Pro25G)  (SEQ ID NO:01)
   ------------------------
5'-GGTCAGTGTATCCAGTTTCTCCGAA-3'  (EQCP1)   (SEQ ID NO:03)
   ------------------------
5'-TCAGGTCAGTGATTCACCGAATCTG-3'  (EQCP2)   (SEQ ID NO:06)
   ------------------------
5'-CAGTCAACCCAGACAGGAACGGAGT-3'  (EQCP3)   (SEQ ID NO:07)
```

Note that both sequences EQCP2 and EQCP3 have been written out because, once EQCP2 has been finalized, EQCP3 is also completely determined.

Do the candidate sequences meet the requirements of nearly equivalent duplex melting temperatures, low self-structure, low composite probe self structure and low cross-hybridization potential? The sequences, predicted duplex melting temperatures and self-structures of the four targets complementary to the candidate probes are shown in Table 2, below.

TABLE 2

| Name | Sequence | Duplex $T_m$ (° C.)[1] | $\Delta G_{self}$ @ 60° C. (kcal/mole)[2] |
|---|---|---|---|
| Tar25C | GGATACACTGACCAGCTACGATGAT (SEQ ID NO:08) | 63.9 | +1.9 |
| EQCT1 | TTCGGAGAAACTGGATACACTGACC (SEQ ID NO:03) | 64.7 | +1.0 |
| EQCT2 | CAGATTCGGTGAATCACTGACCTGA (SEQ ID NO:06) | 64.7 | +0.3 |

TABLE 2-continued

| Name | Sequence | Duplex $T_m$ (° C.)[1] | $\Delta G_{self}$ @ 60° C. (kcal/mole)[2] |
|---|---|---|---|
| EQCT3 | ACTCCGTTCCTGTCTGGGTTGACTG (SEQ ID NO:07) | 69.9 | +0.4 |

[1]Assuming a target concentration of 10 pM
[2]Calculated at using the tools provided at the website having an address in which "http:" is before and ".html" is after "//bioweb.pasteur.fr/seganal/interfaces/mfold-simple"

From Table 2, it is clear that the predicted duplex melting temperatures span a range of 6° C., which are reasonably narrow and above the anticipated hybridization temperature of 60° C. The self-structure free energies of all targets are positive at 60° C., indicating that they possess low structure.

The thermodynamic properties of the composite probes are detailed in Table 3. Note that a $T_5$ tether has been added to the 3' end of each probe, reflecting the fact that mistakes in the first 5 bases of a 60-mer microarray probe have virtually no observable consequences.

TABLE 3

| Name | Sequence | $\Delta G_{self}$ @ 60° C. (kcal/mole) |
|---|---|---|
| EQCP1_Pro25G_T5 | GGTCAGTGTATCCAGTTTCTCCGAAATCATCGTAGCTG GTCAGTGTATCCTTTTT (SEQ ID NO:09) | +0.5 |
| Pro25G_EQCP1_T5 | ATCATCGTAGCTGGTCAGTGTATCCGGTCAGTGTATCC AGTTTCTCCGAATTTTT (SEQ ID NO:10) | +0.9 |
| EQCP2_EQCP3_T5 | TCAGGTCAGTGATTCACCGAATCTGCAGTCAACCCAGA CAGGAACGGAGTTTTT (SEQ ID NO:11) | −0.8 |
| EQCP3_EQCP2_T5 | CAGTCAACCCAGACAGGAACGGAGTTCAGGTCAGTGAT TCACCGAATCTGTTTTT (SEQ ID NO:12) | −1.1 |

Table 3 shows that 2 of the 4 composite probe sequences are liable to be unstructured at the hybridization temperature of 60° C. (free energies are positive), while 2 are likely to possess some structure (free energies are negative). However, detailed examination of the predicted structures shows that they involve only 3 to 4 of the 60 bases in the probe. This finding means that most of the probe is available to the target.

Since the rate-limiting step in hybridization is formation of an initiation duplex that is 3 to 4 bases long, and since duplex formation with all 4 targets is highly thermodynamically favored, this small amount of secondary structure should not inhibit target binding.

Cross-hybridization between each probe and the 3 non-complementary members of the target set has been inhibited by the construction method used. The cyclic permutation of Pro25G used to construct EQCP1 limits the maximum overlap between EQCT1 and Pro25G (or EQCP1 and Tar25C) to 13 of 25 bases. The methods used to construct EQCP2 and EQCP3 are even more destructive to potential cross-hybridization. The result is low predicted cross-hybridization potential.

The cross-hybridization potential between these targets and probes designed against every gene in yeast has been evaluated, using the sequence homology search application BLAST. The results are summarized in Table 4.

TABLE 4

| Control Target Name | Gene Name of Yeast X-hyb Top Score | Yeast X-hyb Top Score Gene Overlap Region | Length of Overlap Region | Yeast Array Probe Sequence Region | POD probe sequence and X-hyb region overlap? |
|---|---|---|---|---|---|
| TAR25C | YNL018c | 1189-1208 | 20 | 1574-1634 | No |
| EQCT1 | YCR086w | 97-114 | 18 | 431-491 | No |
| EQCT2 | YGL023c | 844-857 | 14 | 1661-1720 | No |
| EQCT3 | YOL030w | 761-775 | 15 | 1392-1451 | No |

It is clear from Table 4 that the longest overlap observed between any target and any region of any yeast ORF was 20/25 bases, which is usually sufficiently mismatched to suppress cross-hybridization. More importantly, none of the observed matches actually overlapped a probe on the array. A similar BLAST search against human genes in GenBank yielded no BLAST matches that met the minimum stringency set for the search.

Finally, it should be noted that this method of probe set construction can be generalized to longer sequences (to cover more or all of the layers of a 60-mer array) or to more than 2 labels (with increases in efficiency, since M labels implies that each probe can bind M targets).

It is evident from the above discussion that the above-described invention provides an efficient sampling of the entire area of a microarray. The sampling takes into account the details of the pulse-jet printing process. The sampling patterns can be used for any probe type: positive control, negative control or experimental. The patterns of positive and negative control probes described in this disclosure can be used to correct gradients in hybridization efficiency and background signal binding, respectively. The method provides sequences that gather synthetic efficiency information from most or all layers of a microarray bearing probes appreciably longer than 25 nucleotides. The method uses a minimal set of probes to accomplish this, and therefore saves array features for use by the experimenter, without compromising quality measurements. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing a nucleic acid microarray comprising two or more different nucleic acids immobilized at different locations on a surface, said method comprising:
   (a) identifying a collection of feature locations of the nucleic acid microarray in which to produce control probes during synthesis of the nucleic acid microarray using an in situ microarray synthesis protocol, wherein said protocol utilizes a pulse-jet fluid deposition device having a total number of nozzle groups Y that traverse an entire array surface in one or more passes during said protocol, wherein each pass of said protocol is made up of a total number of swaths Z, and wherein said collection of feature locations samples less than all of said nozzle groups Y in any given swath but all of said nozzle groups Y in said total number of swaths Z of any given pass; and
   (b) producing said nucleic acid microarray using said in situ microarray synthesis protocol, wherein said control probes are produced in said collection of feature locations.

2. The method according to claim 1, wherein said collection of feature locations is made up of a collection of columns.

3. The method according to claim 1, wherein said collection of feature locations make up a regular pattern.

4. The method according to claim 1, wherein said collection of feature locations make up a random pattern.

5. The method according to claim 1, wherein less than about 50% of the total number of groups Y is sampled in any given swath.

6. The method according to claim 1, wherein the same collection of feature locations is employed for printing control probes in each pass of said protocol.

7. A method for producing a nucleic acid microarray having a nucleic acid microarray layout, wherein said nucleic acid microarray comprises test probes and control probes, and wherein said method comprises:
   (a) selecting a collection of columns of said nucleic acid microarray layout in which to produce said control probes during synthesis of said nucleic acid microarray using an in situ microarray synthesis protocol, wherein said nucleic acid microarray layout has a total number of columns X and said in situ microarray synthesis protocol utilizes a pulse-jet fluid deposition device having a total number of nozzle groups Y, and wherein said selecting comprises
   identifying a column pattern period that either:
      (i) shares no prime factors with Y and when multiplied by Y produces a product that does not exceed X; or
      (ii) shares a single prime factor of 2 with Y and when multiplied by Y produces a product that does not exceed X;
   employing said column pattern period to select said collection of columns of said nucleic acid microarray layout in which to produce said control probes; and
   (b) producing said nucleic acid microarray using said in situ microarray synthesis protocol, wherein said control probes are produced in said collection of columns.

8. The method according to claim 7, wherein said pattern period shares no prime factors with Y.

9. The method according to claim 7, wherein said method further comprises selecting an initial column in which to print control probes that results in control probes being printed in substantially the same number of replicate columns per nozzle group.

10. The method according to claim 7, wherein said pattern period shares a single prime factor of 2 with Y.

11. The method according to claim 10, wherein said employing comprises selecting a first collection of columns in which to print control probes and then a second collection of columns in which to print control probes, wherein said second collection of columns has an initial column that is adjacent to the initial column of said first collection of columns.

12. The method according to claim 7, wherein Y is an integer ranging from about 5 to about 50.

13. The method according to claim 7, wherein X is an integer ranging from about 50 to about 1024.

14. The method according to claim 7, wherein each nozzle group making up said total number Y is made up of 6 individual nozzles.

* * * * *

```
                      SEQUENCE LISTING

<160> NUMBER OF SEQ ID NOS: 12

<210> SEQ ID NO 1
<211> LENGTH: 25
<212> TYPE: DNA
<213> ORGANISM: human

<400> SEQUENCE: 1
atcatcgtag ctggtcagtg tatcc                                          25

<210> SEQ ID NO 2
<211> LENGTH: 25
<212> TYPE: DNA
<213> ORGANISM: human

<400> SEQUENCE: 2
ggtcagtgta tccatcatcg tagct                                          25

<210> SEQ ID NO 3
<211> LENGTH: 25
<212> TYPE: DNA
<213> ORGANISM: human

<400> SEQUENCE: 3
ggtcagtgta tccagtttct ccgaa                                          25

<210> SEQ ID NO 4
<211> LENGTH: 25
<212> TYPE: DNA
<213> ORGANISM: human

<400> SEQUENCE: 4
actggtcgat gctactacct atgtg                                          25

<210> SEQ ID NO 5
<211> LENGTH: 25
<212> TYPE: DNA
<213> ORGANISM: human

<400> SEQUENCE: 5
tcaggtcagt gattcaccgt atctg                                          25

<210> SEQ ID NO 6
```

```
<211> LENGTH: 25
<212> TYPE: DNA
<213> ORGANISM: human

<400> SEQUENCE: 6
tcaggtcagt gattcaccga atctg                                              25

<210> SEQ ID NO 7
<211> LENGTH: 25
<212> TYPE: DNA
<213> ORGANISM: human

<400> SEQUENCE: 7
cagtcaaccc agacaggaac ggagt                                              25

<210> SEQ ID NO 8
<211> LENGTH: 25
<212> TYPE: DNA
<213> ORGANISM: human

<400> SEQUENCE: 8
ggatacactg accagctacg atgat                                              25

<210> SEQ ID NO 9
<211> LENGTH: 55
<212> TYPE: DNA
<213> ORGANISM: human

<400> SEQUENCE: 9
ggtcagtgta tccagtttct ccgaaatcat cgtagctggt cagtgtatcc ttttt            55

<210> SEQ ID NO 10
<211> LENGTH: 55
<212> TYPE: DNA
<213> ORGANISM: human

<400> SEQUENCE: 10
atcatcgtag ctggtcagtg tatccggtca gtgtatccag tttctccgaa ttttt            55

<210> SEQ ID NO 11
<211> LENGTH: 55
<212> TYPE: DNA
<213> ORGANISM: human

<400> SEQUENCE: 11
tcaggtcagt gattcaccga atctgcagtc aacccagaca ggaacggagt ttttt            55

<210> SEQ ID NO 12
<211> LENGTH: 55
<212> TYPE: DNA
<213> ORGANISM: human

<400> SEQUENCE: 12
cagtcaaccc agacaggaac ggagttcagg tcagtgattc accgaatctg ttttt            55
```